United States Patent [19]

Smith

[11] 4,211,884
[45] Jul. 8, 1980

[54] 2-DECARBOXY-2-HYDROXYMETHYL-3,7-INTER-m-PHENYLENE-13,14-DIDEHYDRO-PGF COMPOUNDS

[75] Inventor: Herman W. Smith, Kalamazoo, Mich.

[73] Assignee: The Upjohn Company, Kalamazoo, Mich.

[21] Appl. No.: 880,739

[22] Filed: Feb. 24, 1978

Related U.S. Application Data

[62] Division of Ser. No. 814,500, Jul. 11, 1977, Pat. No. 4,134,921, which is a division of Ser. No. 708,752, Jul. 26, 1976, Pat. No. 4,058,564.

[51] Int. Cl.$^2$ ............................................. C07C 35/21
[52] U.S. Cl. ........................................................... 568/807
[58] Field of Search ........................................... 568/807

[56] References Cited

U.S. PATENT DOCUMENTS 3,984,400  10/1976  Eggler et al. .................... 560/121

Primary Examiner—Robert Gerstl
Attorney, Agent, or Firm—Robert A. Armitage

[57] ABSTRACT

This invention comprises certain analogs of the prostaglandins in which the C-1 carboxylic is replaced by a primary alcohol and the double bond between C-13 and C-14 is replaced by a triple bond. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

60 Claims, No Drawings

2-DECARBOXY-2-HYDROXYMETHYL-3,7-INTER-m-PHENYLENE-13,14-DIDEHYDRO-PGF COMPOUNDS

The present application is a divisional application of Ser. No. 814,500, filed July 11, 1977, issued as U.S. Pat. No. 4,134,921 on Jan. 16, 1979; which application is a divisional application of Ser. No. 708,752, filed July 26, 1976, issued as U.S. Pat. No. 4,058,564 on Nov. 15, 1977.

The present invention relates to prostaglandin analogs for which the essential material constituting a disclosure therefor is incorporated by reference here from U.S. Pat. No. 4,058,564, issued Nov. 15, 1977.

I claim:

1. A prostaglandin analog of the formula

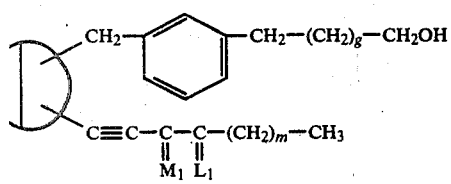

wherein D is

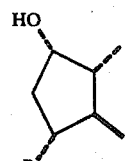

or

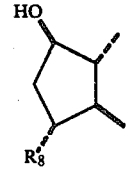

wherein $R_8$ is hydrogen or hydroxy;
wherein $M_1$ is

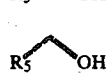

or

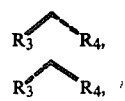

wherein $R_5$ is hydrogen or methyl;
wherein $L_1$ is

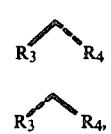

or a mixture of and wherein $R_3$ and $R_4$ are hydrogen, methyl, or fluoro, being the same or different, with the proviso that one of $R_3$ and $R_4$ is fluoro only when the other is hydrogen or fluoro;
wherein g is one, 2, or 3; and
wherein m is one to 5, inclusive.

2. A prostaglandin analog according to claim 1, wherein D is

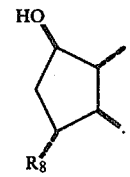

3. A prostaglandin analog according to claim 2, wherein $M_1$ is

4. 2-Decarboxy-2-hydroxymethyl-15-epi-3,7-inter-m-phenylene-4,5,6-trinor-13,14-didehydro-PGF$_1\beta$, a prostaglandin analog according to claim 3.

5. A prostaglandin analog according to claim 2, wherein $M_1$ is

6. A prostaglandin analog according to claim 5, wherein m is 3.

7. A prostaglandin analog according to claim 6, wherein g is 3.

8. 2-Decarboxy-2-hydroxymethyl-2a,2b-dihomo-3,7-inter-m-phenylene-4,5,6-trinor-15-methyl-13,14-didehydro-PGF$_1\beta$, a prostaglandin analog according to claim 7.

9. 2-Decarboxy-2-hydroxymethyl-2a,2b-dihomo-3,7-inter-m-phenylene-4,5,6-trinor-13,14-didehydro-PGF$_1\beta$, a prostaglandin analog according to claim 7.

10. A prostaglandin analog according to claim 6, wherein g is 1.

11. A prostaglandin analog according to claim 10, wherein at least one of $R_3$ and $R_4$ is methyl.

12. A prostaglandin analog according to claim 11, wherein $R_3$ and $R_4$ are both methyl.

13. 2-Decarboxy-2-hydroxymethyl-16,16-dimethyl-3,7-inter-m-phenylene-4,5,6-trinor-13,14-didehydro-PGF$_1\beta$, a prostaglandin analog according to claim 12.

14. A prostaglandin analog according to claim 10, wherein at least one of $R_3$ and $R_4$ is fluoro.

15. A prostaglandin analog according to claim 14, wherein $R_3$ and $R_4$ are both fluoro.

16. 2-Decarboxy-2-hydroxymethyl-3,7-inter-m-phenylene-4,5,6-trinor-16,16-difluoro-13,14-didehydro-PGF$_1\beta$, a prostaglandin analog according to claim 1.

17. A prostaglandin analog according to claim 10, wherein $R_3$ and $R_4$ are both hydrogen.

18. A prostaglandin analog according to claim 17, wherein $R_5$ is methyl.

19. 2-Decarboxy-2-hydroxymethyl-3,7-inter-m-phenylene-4,5,6-trinor-15-methyl-13,14-didehydro-PGF$_1\beta$, a prostaglandin analog according to claim 18.

20. A prostaglandin analog according to claim 17, wherein R$_5$ is hydrogen.

21. 2-Decarboxy-2-hydroxymethyl-3,7-inter-m-phenylene-4,5,6-trinor-13,14-didehydro-PGF$_1\beta$, a prostaglandin analog according to claim 20.

22. A prostaglandin analog according to claim 1, wherein D is

23. A prostaglandin analog according to claim 22, wherein M$_1$ is

24. A prostaglandin analog according to claim 23, wherein m is 3.

25. A prostaglandin analog according to claim 23, wherein g is 3.

26. 2-Decarboxy-2-hydroxymethyl-2a,2b-dihomo-3,7-inter-m-phenylene-4,5,6-trinor-15-epi-15-methyl-13,14-didehydro-PGF$_1\beta$, a prostaglandin analog according to claim 25.

27. 2-Decarboxy-2-hydroxymethyl-2a,2b-dihomo-3,7-inter-m-phenylene-4,5,6-trinor-15-epi-13,14-didehydro-PGF$_1\beta$, a prostaglandin analog according to claim 25.

28. A prostaglandin analog according to claim 24, wherein g is 1.

29. A prostaglandin analog according to claim 28, wherein at least one of R$_3$ and R$_4$ is methyl.

30. 2-Decarboxy-2-hydroxymethyl-15-epi-3,7-inter-m-phenylene-4,5,6-trinor-16,16-dimethyl-13,14-didehydro-PGF$_1\beta$, a prostaglandin analog according to claim 29.

31. A prostaglandin analog according to claim 28, wherein at least one of R$_3$ and R$_4$ is fluoro.

32. 2-Decarboxy-2-hydroxymethyl-3,7-inter-m-phenylene-4,5,6-trinor-15-epi-16,16-difluoro-13,14-didehydro-PGF$_1\beta$, a prostaglandin analog according to claim 31.

33. A prostaglandin analog according to claim 28, wherein R$_3$ and R$_4$ are both hydrogen.

34. 2-Decarboxy-2-hydroxymethyl-3,7-inter-m-phenylene-4,5,6-trinor-15-epi-15-methyl-13,14-didehydro-PGF$_1\beta$, a prostaglandin analog according to claim 33.

35. A prostaglandin analog according to claim 22, wherein M$_1$ is

36. A prostaglandin analog according to claim 35, wherein m is 3.

37. A prostaglandin analog according to claim 36, wherein g is 3.

38. A prostaglandin analog according to claim 37, wherein at least one of R$_3$ and R$_4$ is methyl.

39. 2-Decarboxy-2-hydroxymethyl-2a,2b-dihomo-3,7-inter-m-phenylene-4,5,6-trinor-16,16-dimethyl-13,14-didehydro-PGF$_1\beta$, a prostaglandin analog according to claim 38.

40. A prostaglandin analog according to claim 37, wherein at least one of R$_3$ and R$_4$ is fluoro.

41. 2-Decarboxy-2-hydroxymethyl-2a,2b-dihomo-3,7-inter-m-phenylene-4,5,6-trinor-16,16-difluoro-13,14-didehydro-PGF$_1\beta$, a prostaglandin analog according to claim 40.

42. A prostaglandin analog according to claim 37, wherein R$_3$ and R$_4$ are both hydrogen.

43. 2-Decarboxy-2-hydroxymethyl-2a,2b-dihomo-3,7-inter-m-phenylene-4,5,6-trinor-15-methyl-13,14-didehydro-PGF$_1\beta$, a prostaglandin analog according to claim 42.

44. A prostaglandin analog according to claim 36, wherein g is 1.

45. A prostaglandin analog according to claim 44, wherein at least one of R$_3$ and R$_4$ is methyl.

46. A prostaglandin analog according to claim 45, wherein only one of R$_3$ and R$_4$ is methyl.

47. 2-Decarboxy-2-hydroxymethyl-3,7-inter-m-phenylene-4,5,6-trinor-16-methyl-13,14-didehydro-PGF$_2\beta$, a prostaglandin analog according to claim 46.

48. A prostaglandin analog according to claim 45, wherein R$_3$ and R$_4$ are both methyl.

49. 2-Decarboxy-2-hydroxymethyl-3,7-inter-m-phenylene-4,5,6-trinor-16,16-dimethyl-13,14-didehydro-PGF$_1\beta$, a prostaglandin analog according to claim 48.

50. A prostaglandin analog according to claim 44, wherein at least one of R$_3$ and R$_4$ is fluoro.

51. A prostaglandin analog according to claim 50, wherein R$_3$ and R$_4$ are both fluoro.

52. A prostaglandin analog according to claim 51, wherein R$_5$ is methyl.

53. 2-Decarboxy-2-hydroxymethyl-3,7-inter-m-phenylene-4,5,6-trinor-15-methyl-16,16-difluoro-13,14-didehydro-PGF$_1\beta$, a prostaglandin analog according to claim 52.

54. A prostaglandin analog according to claim 51, wherein R$_5$ is hydrogen.

55. 2-Decarboxy-2-hydroxymethyl-3,7-inter-m-phenylene-4,5,6-trinor-16,16-difluoro-13,14-didehydro-PGF$_1\beta$, a prostaglandin analog according to claim 54.

56. A prostaglandin analog according to claim 44, wherein R$_3$ and R$_4$ are both hydrogen.

57. A prostaglandin analog according to claim 56, wherein R$_5$ is methyl.

58. 2-Decarboxy-2-hydroxymethyl-3,7-inter-m-phenylene-4,5,6-trinor-15-methyl-13,14-didehydro-PGF$_1\beta$, a prostaglandin analog according to claim 57.

59. A prostaglandin analog according to claim 56, wherein R$_5$ is hydrogen.

60. 2-Decarboxy-2-hydroxymethyl-3,7-inter-m-phenylene-4,5,6-trinor-13,14-dihydro-PGF$_1\beta$, a prostaglandin analog according to claim 59.

* * * * *

UNITED STATES PATENT OFFICE
CERTIFICATE OF CORRECTION

Patent No. 4,211,884                 Dated  8 July 1980

Inventor(s)  Herman W. Smith

It is certified that error appears in the above-identified patent and that said Letters Patent are hereby corrected as shown below:

Column 4, lines 7, 13, 19, 34, 43, 49, 55, and 60, "$PGF_1\beta$," should read -- $PGF_1\alpha$, --.

Column 4, line 28, "$PGF_2\beta$" should read -- $PGF_2\alpha$ --.

Signed and Sealed this

Twelfth Day of May 1981

[SEAL]

Attest:

RENE D. TEGTMEYER

Attesting Officer

Acting Commissioner of Patents and Trademarks